(12) United States Patent  
Piccagli

(10) Patent No.: US 9,272,121 B2  
(45) Date of Patent: Mar. 1, 2016

(54) SIDE LUMEN REENTRY CATHETERS AND RELATED METHODS

(71) Applicant: Invatec S.p.A., Roncadelle (IT)

(72) Inventor: Francesco Piccagli, Roncadelle (IT)

(73) Assignee: Invatec S.p.a., Roncadelle, BS (IT)

( * ) Notice: Subject to any disclaimer, the term of this patent is extended or adjusted under 35 U.S.C. 154(b) by 471 days.

(21) Appl. No.: 13/799,949

(22) Filed: Mar. 13, 2013

(65) Prior Publication Data

US 2014/0275983 A1    Sep. 18, 2014

(51) Int. Cl.
| | |
|---|---|
| *A61M 25/01* | (2006.01) |
| *A61M 25/09* | (2006.01) |
| *A61M 25/10* | (2013.01) |
| *A61B 17/22* | (2006.01) |
| *A61B 17/3207* | (2006.01) |

(52) U.S. Cl.
CPC ............ *A61M 25/0194* (2013.01); *A61B 17/22* (2013.01); *A61B 17/3207* (2013.01); *A61M 25/0108* (2013.01); *A61M 25/09* (2013.01); *A61M 25/104* (2013.01)

(58) Field of Classification Search
CPC ............ A61M 25/0194; A61M 25/09; A61M 25/104; A61M 25/0108; A61B 17/3207; A61B 17/22
See application file for complete search history.

(56) References Cited

U.S. PATENT DOCUMENTS

| | | | |
|---|---|---|---|
| 5,830,222 A | 11/1998 | Makower | |
| 6,068,638 A | 5/2000 | Makower | |
| 6,159,225 A | 12/2000 | Makower | |
| 6,190,353 B1 | 2/2001 | Makower et al. | |
| 6,283,951 B1 | 9/2001 | Flaherty et al. | |
| 6,302,875 B1 * | 10/2001 | Makower ................ | A61B 8/12 604/528 |
| 6,375,615 B1 | 4/2002 | Flaherty et al. | |
| 6,508,824 B1 | 1/2003 | Flaherty et al. | |
| 6,544,230 B1 | 4/2003 | Flaherty et al. | |
| 6,579,311 B1 | 6/2003 | Makower | |
| 6,602,241 B2 | 8/2003 | Makower et al. | |
| 6,655,386 B1 | 12/2003 | Makower et al. | |
| 6,660,024 B1 | 12/2003 | Flaherty et al. | |
| 6,685,648 B2 | 2/2004 | Flaherty et al. | |
| 6,709,444 B1 | 3/2004 | Makower | |
| 6,726,677 B1 | 4/2004 | Flaherty et al. | |

(Continued)

FOREIGN PATENT DOCUMENTS

| | | |
|---|---|---|
| EP | 1690563 | 8/2006 |
| EP | 2138200 | 12/2009 |

(Continued)

OTHER PUBLICATIONS

Jaffan A.A., et al. Balloon Occlusion of Subintimal Tract to Assist Distal Luminal Reentry Into Popliteal Artery, J Vasc Intery Radiol. Oct. 2012; 23(10): 1389-91.

(Continued)

*Primary Examiner* — Bo J Peng

(57) ABSTRACT

True lumen reentry devices and methods useable for redirecting a guidewire from a subintimal tract within a wall of a blood vessel into the true lumen of the blood vessel. A reentry catheter device comprises a main catheter shaft having at least one guidewire outlet aperture with at least one side tube located on a distal portion of the main catheter shaft. The side tube(s) is/are tracked over initially inserted guidewire(s) to advance a distal portion of the reentry catheter device into the subintimal tract with a guidewire.

21 Claims, 15 Drawing Sheets

(56) References Cited

U.S. PATENT DOCUMENTS

| | | |
|---|---|---|
| 6,746,464 B1 | 6/2004 | Makower |
| 7,645,273 B2 | 1/2010 | Lualdi |
| 7,938,819 B2 | 5/2011 | Kugler et al. |
| 8,043,314 B2 | 10/2011 | Noriega et al. |
| 8,083,727 B2 | 12/2011 | Kugler et al. |
| 8,241,311 B2 | 8/2012 | Ward et al. |
| 8,257,382 B2 | 9/2012 | Rottenberg et al. |
| 8,323,261 B2 | 12/2012 | Kugler et al. |
| 8,337,425 B2 | 12/2012 | Olson et al. |
| 8,353,922 B2 | 1/2013 | Noriega et al. |
| 2007/0010840 A1 | 1/2007 | Rosenthal |
| 2007/0293846 A1* | 12/2007 | von Oepen ........ A61M 25/0029 604/529 |
| 2010/0280450 A1 | 11/2010 | Jain |

FOREIGN PATENT DOCUMENTS

| | | |
|---|---|---|
| WO | WO97/13463 | 4/1997 |
| WO | WO2013/003757 | 1/2013 |

OTHER PUBLICATIONS

PCT/US2014/017188, PCT Search Report and Written Opinion, mailed Apr. 24, 2014.

* cited by examiner

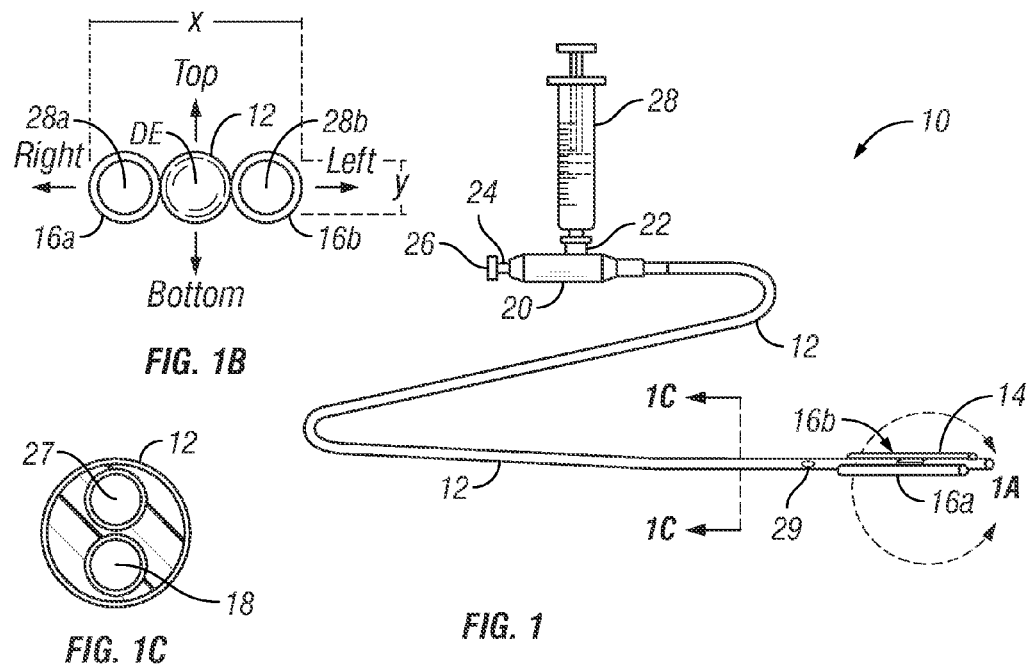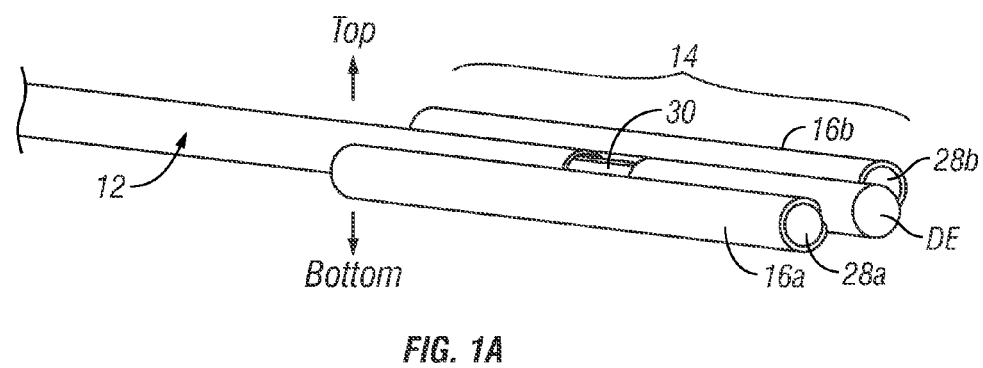

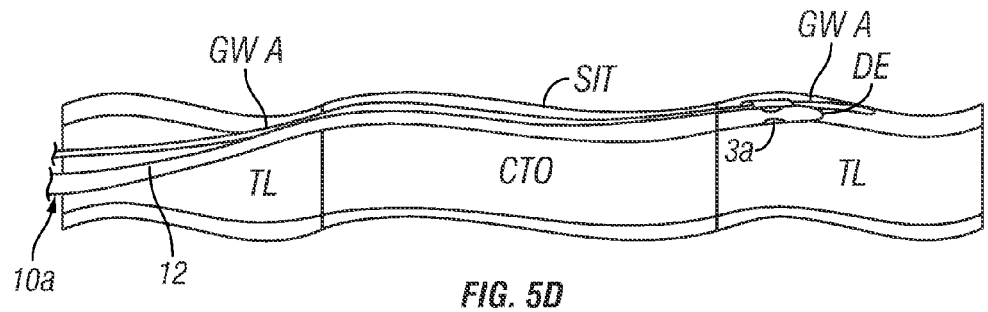
FIG. 5D
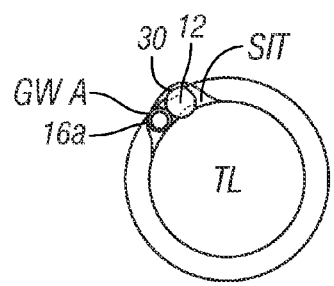
FIG. 5D-1
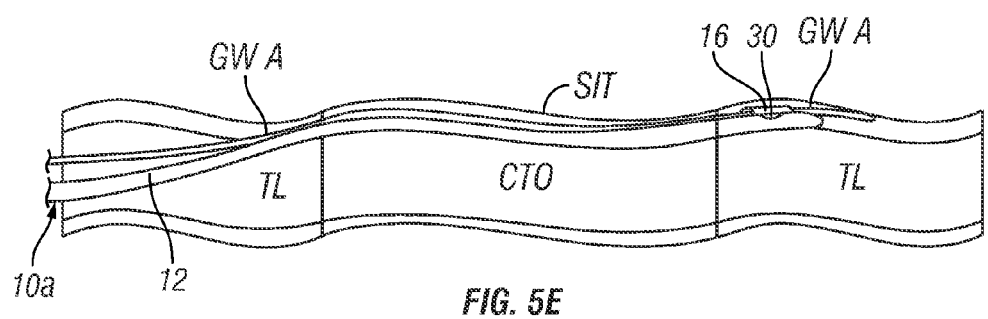
FIG. 5E
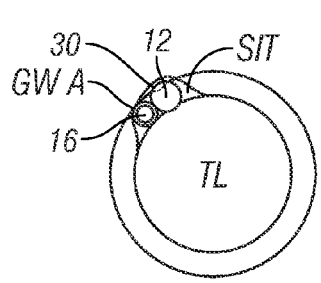    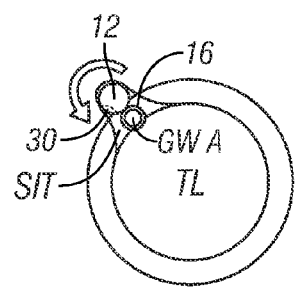    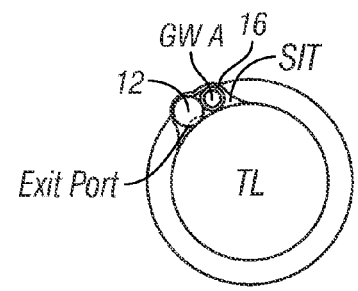
FIG. 5E-1          FIG. 5E-2          FIG. 5E-3

SIDE LUMEN REENTRY CATHETERS AND RELATED METHODS

FIELD OF THE INVENTION

The present invention relates generally to the fields of mechanical engineering and medicine and more particularly to apparatus and methods for directing the advancement of catheters and other elongate medical devices.

BACKGROUND

In various medical procedures, it is desirable to direct a guidewire or other elongate medical device from one location to another location within the body of a human or non-human animal subject. For example, during endovascular treatment of chronic total occlusions (CTOs) of arteries, a guidewire may sometimes penetrate into and become embedded within the wall of the occluded artery (i.e., creating a "subintimal space" or "subintimal tract"). Often, a distal portion of the guidewire is tightly looped as it is advanced into the artery wall, thereby causing a blunt dissection or separation between tissue layers and forming a subintimal tract that has the shape of a flat or curved slit. Various reentry devices and strategies have been employed to re-direct the distal portion of the guidewire from its position within the newly-formed subintimal tract, back into the true lumen of the artery. Once the guidewire has been re-directed into the true lumen of the artery distal to the obstruction, that guidewire may then be used to facilitate the use of other catheter based devices to enlarge and stent the newly-formed subintimal tract, thereby establishing a new blood flow channel around the obstruction.

The prior art has included a number of true lumen reentry devices that are potentially useable to redirect a subintimally entrapped guidewire into the true lumen of the artery. Commercial examples of such reentry devices include the Pioneer® Catheter (Medtronic Vascular, Santa Rosa, Calif.); the OUTBACK® LTD® Reentry Catheter (Cordis Corporation, Miami, Fla.) and the Enteer™ Reentry System (Covidien/eV3, Plymouth, Minn.). Other examples are described in U.S. Pat. No. 5,830,222 (Makower); U.S. Pat. No. 6,068,638 (Makower); U.S. Pat. No. 6,159,225 (Makower); U.S. Pat. No. 6,190,353 (Makower, et al.); U.S. Pat. No. 6,283,951 (Flaherty, et al.); U.S. Pat. No. 6,375,615 (Flaherty, et al.); U.S. Pat. No. 6,508,824 (Flaherty, et al.); U.S. Pat. No. 6,544,230 (Flaherty, et al.); U.S. Pat. No. 6,655,386 (Makower et al.); U.S. Pat. No. 6,579,311 (Makower); U.S. Pat. No. 6,602,241 (Makower, et al.); U.S. Pat. No. 6,655,386 (Makower, et al.); U.S. Pat. No. 6,660,024 (Flaherty, et al.); U.S. Pat. No. 6,685,648 (Flaherty, et al.); U.S. Pat. No. 6,709,444 (Makower); U.S. Pat. No. 6,726,677 (Flaherty, et al.); U.S. Pat. No. 6,746,464 (Makower); U.S. Pat. No. 7,938,819 (Kugler, et al.); U.S. Pat. No. 8,323,261 (Kugler, et al.); U.S. Pat. No. 8,083,727 (Kugler, et al.); U.S. Pat. No. 8,241,311 (Ward et al.); U.S. Pat. No. 8,257,382 (Rottenberg, et al.); U.S. Pat. No. 8,337,425 (Olson et al.); U.S. Pat. No. 8,353,922 (Noriega, et al.) and U.S. Pat. No. 8,043,314 (Noriega, et al.).

Additionally, a recent published report describes the use of a balloon occlusion technique for diverting a guidewire from a subintimal tract into the true lumen of an artery, in lieu of using a reentry catheter. In this reported case, a 0.035 inch guidewire was initially used to form the subintimal tract that extended past an obstructive lesion. That 0.035 inch guidewire was then removed and a separate 0.018 inch guidewire was selectively advanced into the subintimal tract. A low-profile balloon catheter was then advanced over the 0.018 inch wire into the subintimal tract. The balloon was inflated to block the subintimal tract. A 0.035 inch guidewire was then advanced through the subintimal tract next to the balloon catheter. The presence of inflated balloon within the subintimal tract caused the advancing 0.035 inch guidewire to divert out of the initial subintimal tract and into the true lumen of the artery, distal to the obstruction. Although this procedure did successfully cause the 0.035 inch guidewire to re-enter the true lumen of the artery without use of a separate reentry catheter, this procedure did involve several time consuming steps and required the use of several guidewires as well as a separate balloon catheter. Additionally, as the authors note, this procedure must be performed with caution as advancement of the 0.035 inch guidewire past the inflated balloon could result in inadvertent perforation of the artery with resultant hematoma or arteriovenous fistula formation. Jaffan A. A., et al., *Balloon Occlusion Of Subintimal Tract To Assist Distal Luminal Reentry Into Popliteal Artery*, J Vasc Interv Radiol. 2012 October; 23(10):1389-91.

There remains a need in the art for the development of different and improved devices and methods useable for redirecting a subintimally entrapped guidewire back into the true lumen of an artery in a safe and efficient manner.

SUMMARY OF THE INVENTION

The present invention provides devices and methods useable for directing a guidewire or other elongate device from one location to another location within a subject's body. The invention includes devices and methods for directing a guidewire or other elongate device (e.g., a wire, probe, catheter, etc.) from a location within the wall of a blood vessel into the adjacent true lumen of that blood vessel.

In accordance with the present invention, there are provided lumen reentry devices and their methods of use. Lumen reentry devices of this invention generally comprise a catheter having an elongate flexible catheter shaft and a main guidewire lumen extending through the catheter shaft in communication with one or more guidewire exit aperture(s). One or more side tube(s) having lumen(s) is/are present on a distal portion of the catheter shaft. After at least a first guidewire has been advanced into a subintimal tract within an artery wall, a side tube lumen of a reentry catheter side tube is advanced over that guidewire until the distal portion of the reentry catheter device is positioned within the subintimal tract with a guidewire exit aperture directed toward the adjacent true lumen of the artery. Thereafter, a second or additional guidewire is advanced through the main guidewire lumen of the reentry catheter shaft, out of the guidewire exit aperture directed toward the artery's true lumen and into the true lumen. The reentry catheter and first guidewire may then be removed, leaving the second guidewire in place.

Still further aspects, details and embodiments of the present invention will be understood by those of skill in the art upon reading the following detailed description of the invention and the accompanying drawings.

BRIEF DESCRIPTION OF THE DRAWINGS

FIG. 1A is a perspective view of portion 1A of FIG. 1.

FIG. 1B is a distal end view of the device of FIG. 1.

FIG. 1C is a transverse sectional view through line 1C-1C of FIG. 1.

FIGS. 5A-5G show steps in a method for using another embodiment of a reentry catheter of the present invention to facilitate a transluminal catheter-based bypass of a CTO in an artery.

DETAILED DESCRIPTION

The following detailed description and the accompanying figures are intended to describe and show some, but not necessarily all, examples or embodiments of the invention. These examples and embodiments are to be considered in all respects only as illustrative and not restrictive. The contents of this detailed description and the accompanying figures do not limit the scope of the claimed invention in any way.

The accompanying figures generally show examples of reentry catheter devices 10, 10a of the present invention and their methods of use.

Reentry Catheter Having Dual Side Tubes

Figure 1E:
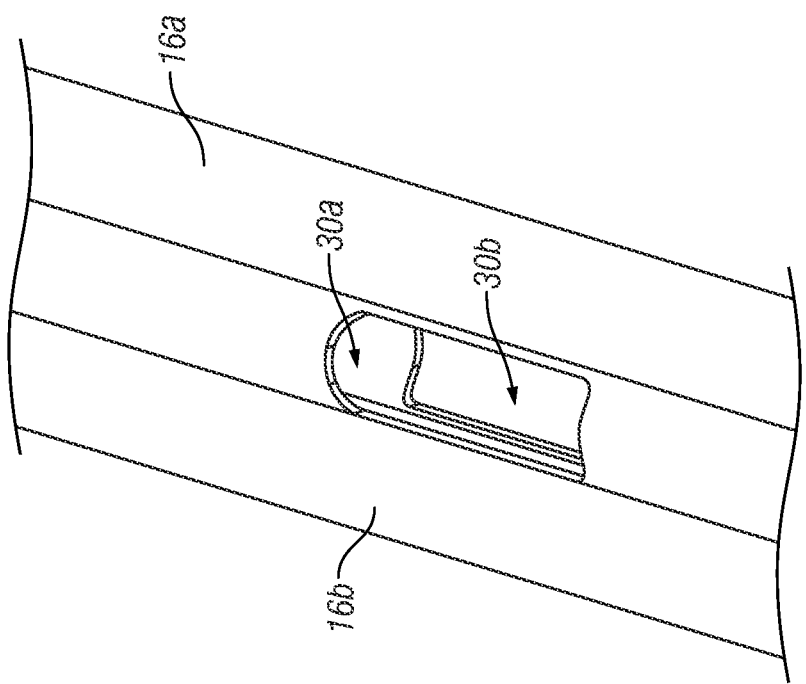
FIG. 1E is a top perspective view of a portion of the device of FIG. 1 equipped with dual (i.e., top and bottom) guidewire exit ports.
Figure 1D:
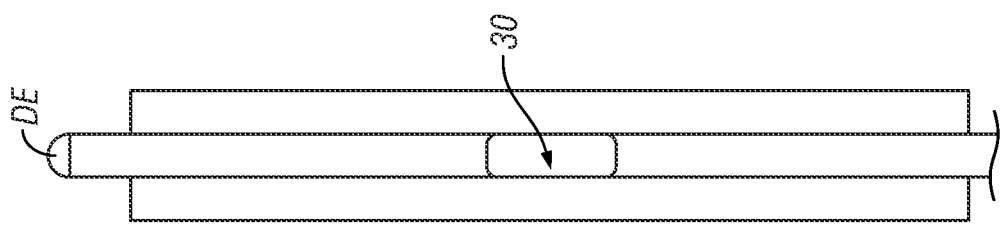
FIG. 1D is a top view of a distal portion of the device of FIG. 1.
Figure 1F:
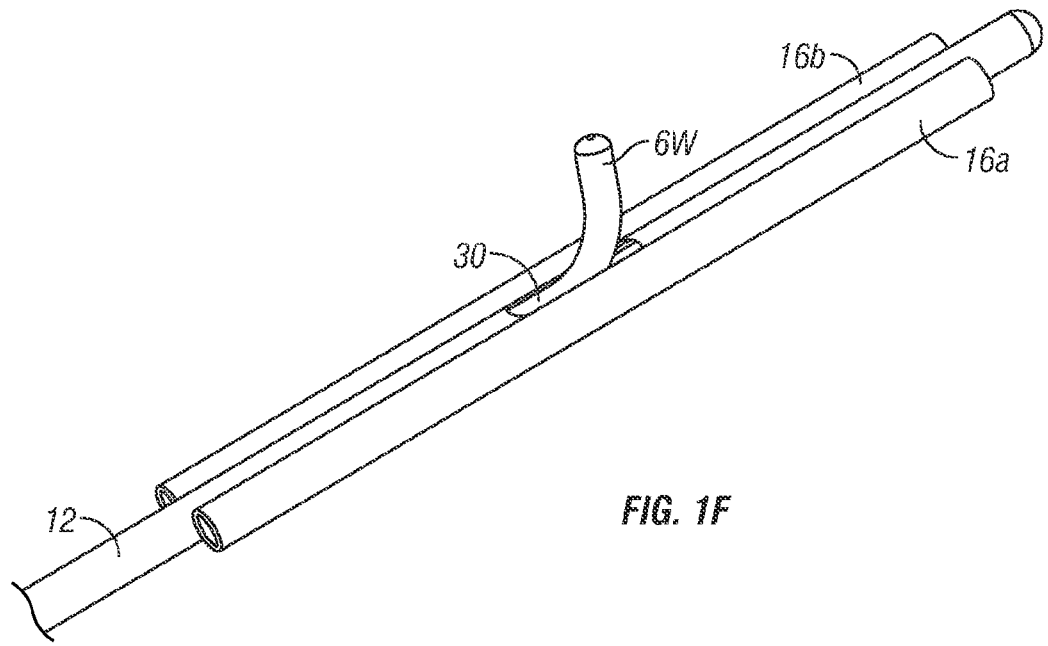
FIG. 1F is a perspective view of a distal portion of the device of FIG. 1 showing a guidewire advancing out of a guidewire exit port.

FIGS. 1 through 1I and 4A through 4H refer to an example of a reentry catheter device 10 that has a main catheter shaft 12 and dual side tubes 16a, 16b attached to a distal portion 14 of the main catheter shaft 12. As labeled on FIG. 1B, the distal portion 14 of the catheter shaft to which the side tubes 16a, 16b are attached has a right side (on which the first side tube 16a is located), a left side (on which the second side tube 16b is located), a top side and a bottom side. The length of the side tubes can vary depending on length of the guidewire portion that is to be supported for stable guidance and tracking of the catheter distal end. Moreover, the length of the side tubes can vary depending on length of the occlusion to be treated; typically, long occlusions are preferably treated by using long side tubes. The side tubes 16a, 16b have open proximal and distal ends such that a lumen 28a, 28b extends longitudinally directly through each side tube 16a, 16b. The side tubes 16a, 16b occupy symmetrical positions on the right and left sides of the main catheter shaft 12. As noted in FIG. 1B, the transverse (width) dimension X of the distal portion 14 is greater than its vertical (height) dimension Y. According to the embodiment shown in the figures the transverse dimensions of side tubes 16a, 16b are substantially identical to the transverse dimensions of main catheter shaft 12. Alternatively, the transverse dimensions of side tubes 16a, 16b are different from the transverse dimensions of main catheter shaft 12.

The main catheter shaft 12 comprises an elongate, flexible catheter that has a distal end DE and at least a main guidewire lumen 18. The distal end DE of the main catheter shaft 12 may be closed (as shown) or open. One or more guidewire outlet aperture(s) 30 is/are formed in the top side and/or bottom side of the main shaft 12 to permit a guidewire (or other suitable elongate guide member such as a probe, secondary catheter, fiber, etc.) to laterally exit the main catheter shaft 12. The one or more guidewire outlet aperture(s) 30 is/are not covered or obscured by the side tubes 16a, 16b such that a guidewire may be freely advanced out of the guidewire outlet aperture(s) 30. In many applications, it will be desirable for the device 10 to include a first guidewire outlet aperture 30a in the top side of the catheter shaft and a second guidewire outlet aperture 30b in the bottom side of the catheter shaft so that a guidewire may be selectively advanced out of either of such guidewire outlet apertures 30a, 30b depending on which of the top and bottom sides is directed toward the true lumen of the blood vessel, as will be described more fully herebelow. In embodiments that include a first guidewire outlet aperture 30a in the top side of the main catheter shaft 12 and a second guidewire outlet aperture 30b in the bottom side of the main catheter shaft 12, the first and second guidewire outlet apertures 30a, 30b may be positioned at longitudinally spaced apart locations to facilitate selective passage of curved-tipped guidewire GW out of one or the other of these outlet apertures 30a, 30b. Thus, the guidewire GW inserted into the main catheter shaft 12 optionally has a bent (preformed) distal end portion to allow the operator to selectively cause the guidewire GW to exit whichever guidewire outlet aperture 30a, 30b is directed toward the true lumen of the vessel, Once the distal tip of the main guidewire GW has exited the desired guidewire outlet aperture 30a, 30b (see below for how the correct exit port is chosen between the two) the main guidewire GW is pushed and perforates through the intervening intimal tissue and enters the true lumen of the vessel distal to the occlusion. Alternatively, the main catheter shaft 12 may have two separate guidewire lumens, one leading to the top side guidewire outlet aperture 30a and the other leading to the bottom side guidewire outlet aperture 30b.

A proximal hub 20 may be provided on the proximal end of the main catheter shaft 12. In the example shown, the proximal hub 20 has a guidewire port 24 which communicates with the guidewire lumen 18 of the catheter shaft 12. Optionally, a Tuohy Borst valve 26 or other suitable hemostatic valve may be mounted on the guidewire port 24, as shown. Also, an optional second lumen 27 may extend through the catheter shaft 12 to an optional second lumen outlet port 29. In embodiments having such second lumen 27 and second lumen outlet port 29, the proximal hub may also include a second proximal hub port 22 in communication with the second lumen 27. In the example shown, this second proximal hub port 22 comprises a female Luer connector suitable for connection to a syringe, solution administration tube or other apparatus 28 for introducing or withdrawing substances (e.g., radiographic contrast medium, saline solution, medicaments, etc.). In some embodiments, the optional second lumen 27 and second lumen outlet port 29 may alternatively be used for introduction of a secondary device (e.g., a fiberoptic angioscope, cautery wire, etc.) rather than (or in addition to) infusion or withdrawal of a substance.

Figure 1G:
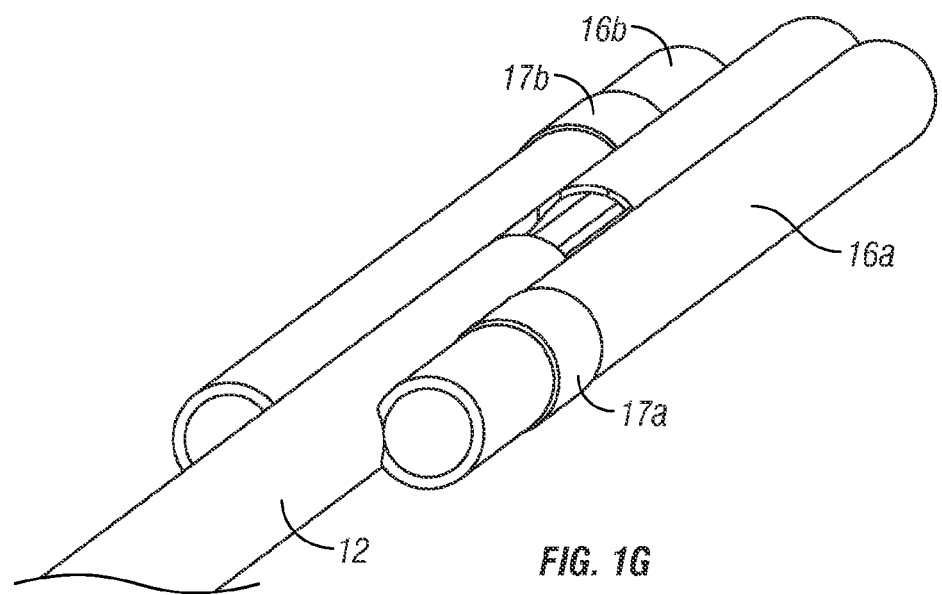
FIG. 1G is a perspective view of a distal portion of the device of FIG. 1 equipped with radiopaque markers.
Figure 1H:
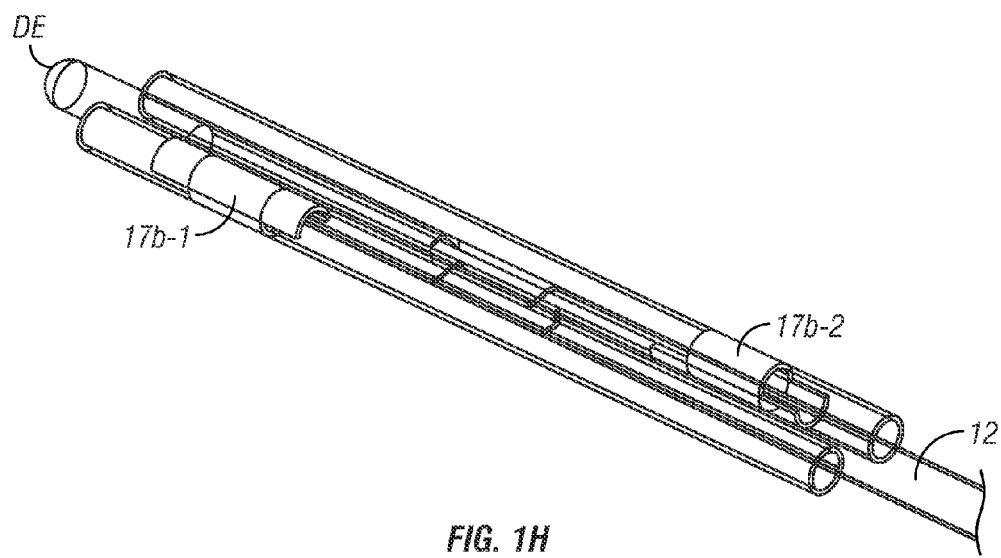
FIG. 1H is a perspective view of a distal portion of the device of FIG. 1 equipped with radiopaque markers that are configured to indicate rotational orientation as well as longitudinal position.
Figure 1I:
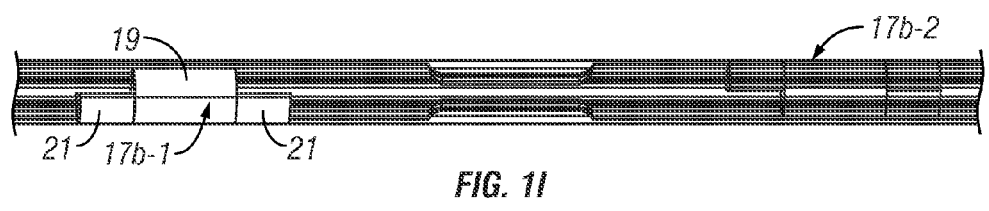
FIG. 1I is a side view of FIG. 1H.

The reentry catheter device 10 may optionally include one or more radiopaque or otherwise imageable markers (e.g., echogenoc structures which ate imageable by ultrasound, signal emitters that emit signals detectable by sensor(s), etc.)

to enhance detection of the device's position and/or rotational orientation within the body. In the example seen in FIG. 1G, the device includes radiopaque marker bands 17a, 17b to enhance visibility of the side tubes 16a, 16b and/or of the main catheter shaft 12 when positioned within a subject's vasculature. In particular, marker bands 17a and 17b may be placed at different longitudinal locations on side tubes 16a, 16b, as shown. Other types of imageable markers may alternatively be used in lieu of, or in addition to, radiopaque markers. Because the marker bands 17a and 17b are placed at different longitudinal locations relative to other radiopaque or imageable landmark(s) on the device 10, these marker bands 17a, 17b may be used by the operator to distinguish the two side tubes 16a, 16b within the vasculature as well as identifying their alignment. Some embodiments may have markers having specific shapes in order to better distinguish the side tubes 16a, 16b and the alignment of the distal portion 14 of the device within the vasculature. For example, as shown in FIGS. 1H and 1I, the marker band 17b-1 on one of the side tubes may be longer at the top side and shorter on the bottom side while the other marker band 17b-2 on the other side tube is shorter on the top side and longer on the bottom side.

To appreciate the advantageous uses of the above-described reentry catheter device 10, it is helpful to understand the disorders it is useable to treat. In many cases, the device 10 may be used to treat a CTO in an artery of the leg which has resulted from uncontrolled Peripheral Arterial Disease (PAD). PAD in a lower limb can cause cramping, intermittent claudication and numbness in the affected leg, especially while walking or during exertion. CTOs in leg arteries are composed of smooth muscle cells, connective tissue, calcium, thrombus, lipids and inflammatory cells. These lesions may be more than 20 cm in length. Often they are heavily calcified or fibrotic.

Figure 2:
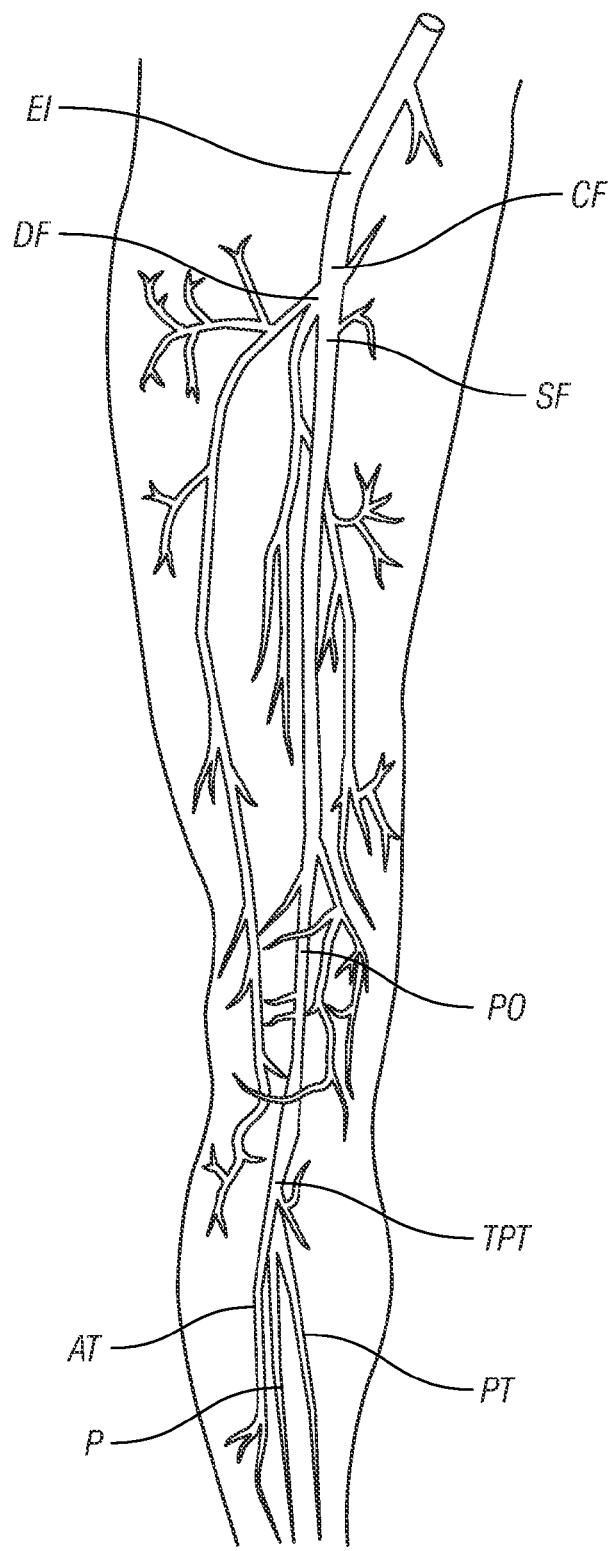
FIG. 2 is a schematic diagram showing arteries of a human leg.

FIG. 2 shows arteries of the human leg, as follows:

| | |
|---|---|
| EI | External Iliac Artery |
| DF | Deep Femoral Artery |
| CF | Circumflex Artery |
| SF | Superficial Femoral Artery |
| PO | Popliteal Artery |
| TPT | Tibioperoneal Trunk |
| AT | Anterior Tibial Artery |
| PT | Posterior Tibial Artery |
| P | Peroneal Artery |

The superficial femoral artery (SF) is a long artery running substantially the length of the thigh. CTOs of the SFA present in up to 50% of the patients treated for PAD. As can be seen from FIG. 2, a CTO of the SF can cause diminished blood flow in numerous other downstream arteries that receive all or part of their arterial blood supply via the SF.

Figure 3:
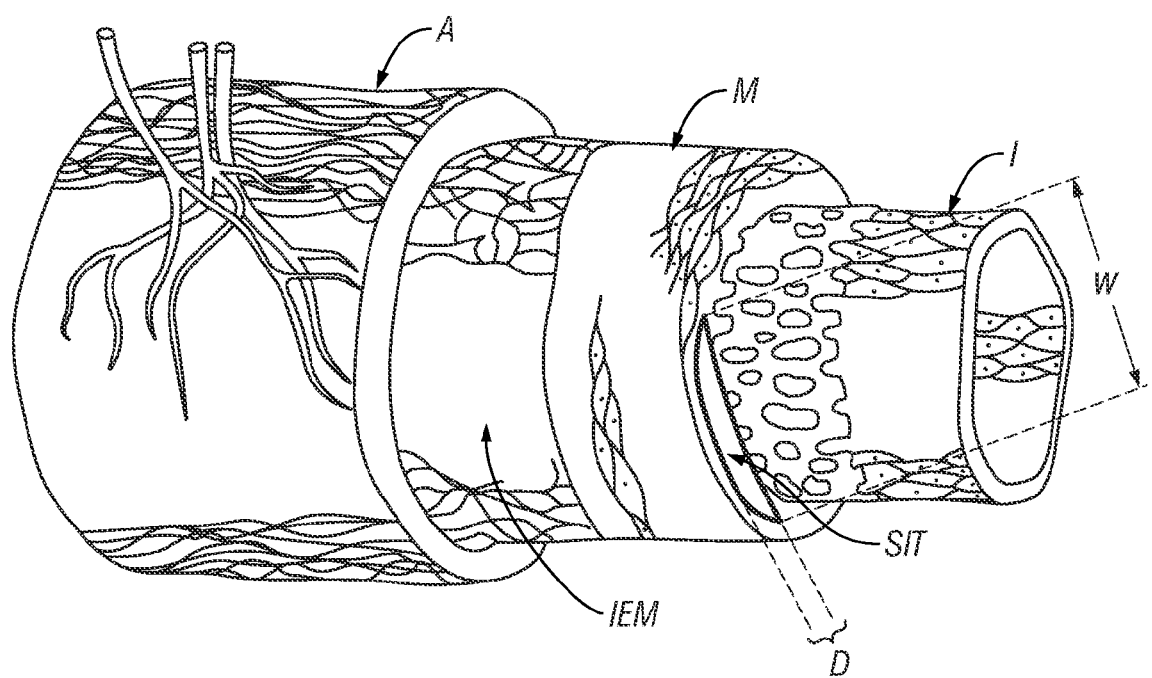
FIG. 3 is an anatomical diagram showing the histological layers of an artery.

FIG. 3 shows that the wall of an artery typically consists of three layers, the tunica intima I ("intima"), tunica media M ("media") and the tunica adventitia A ("adventitia"). In some arteries an internal elastic membrane IEM is disposed between the tunica media M and tunica adventitia A. The tunica intima I is a relatively thin layer of soft, smooth tissue that lines the true lumen of the artery. The tunica media M, which surrounds the intima I, is a thicker layer which includes elastic fibers and smooth muscle. The tunica adventitia A comprises connective tissue which acts as a protective coat around the artery and also helps to attach the artery to adjacent anatomical structures like muscles. When attempting to push a guidewire through a CTO, the distal end of the guidewire sometimes penetrates into the artery wall. When this happens, the guidewire can sometimes be further advanced longitudinally within the artery wall, creating a subintimal tract SIT between the tunica intima I (which is relatively thin and flexible) and the tunica media M (which is thicker and less flexible). Often, the guidewire doubles over as it is being pushed between the tissue layers in the artery wall. As noted in FIG. 3, this typically results in the formation of a subintimal tract SIT that is relatively flat or slightly curved and has a width W greater than its depth D. Thus, as explained in more detail in the working examples below, when the distal portion 14 of reentry catheter device 10 is advanced through a subintimal tract SIT, it will assume an orientation whereby its transverse dimension X extends across the width W of the subintimal tract SIT and its vertical dimension Y extends over the depth D of the subintimal tract SIT. Thus, either the top or bottom side of the main catheter shaft 12 will be directed toward the true lumen of the vessel.

Figure 4A:
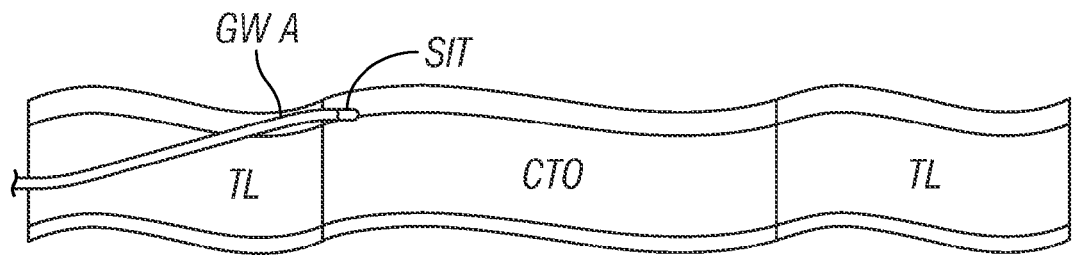
FIGS. 4A-4H show steps in a method for using the reentry catheter of FIG. 1 to facilitate a transluminal catheter-based bypass of a CTO in an artery.
Figures 1, 4A:
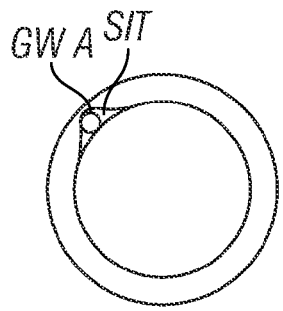
FIG. 1 is a side view of one embodiment of a reentry catheter device of the present invention.

FIGS. 4A through 4H show an example of a method for bypassing a CTO in an artery using the above-described reentry catheter device 10. In this example, the true lumen TL of the artery is blocked by a chronic total obstruction CTO. Initially, as seen in FIGS. 4A and 4A-1, a first auxiliary guidewire GW A is inserted into the patient's vasculature and advanced to the obstruction CTO. At that point, the distal end of the first auxiliary guidewire GW A penetrates into the wall of the artery, adjacent to the proximal end of the obstruction CTO. This begins formation of the subintimal tract SIT within the artery wall.

Figure 4B:
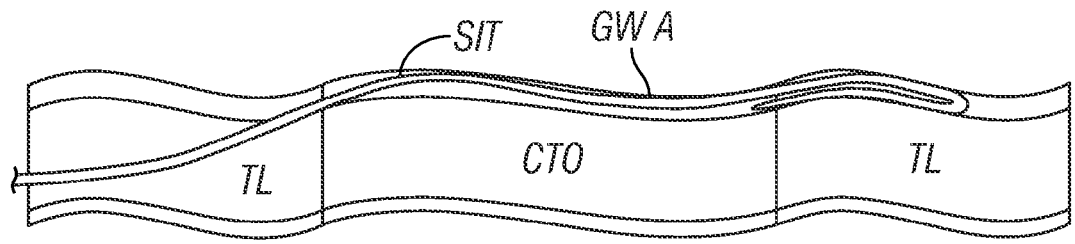
Figures 1, 4B:
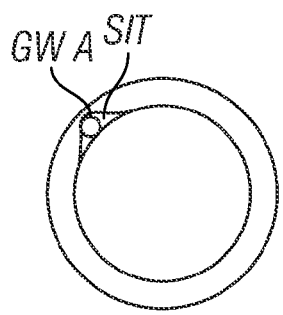

As seen in FIGS. 4B and 4B-1, the first auxiliary guidewire GW A is then further advanced within the artery wall, causing a distal portion of the first auxiliary guidewire GW A to double over in a loop-like form, as shown. This extends the subintimal tract SIT past the obstruction CTO and causes the subintimal tract SIT to have a width W that is wider than its depth D (see FIG. 3).

Figure 4C:
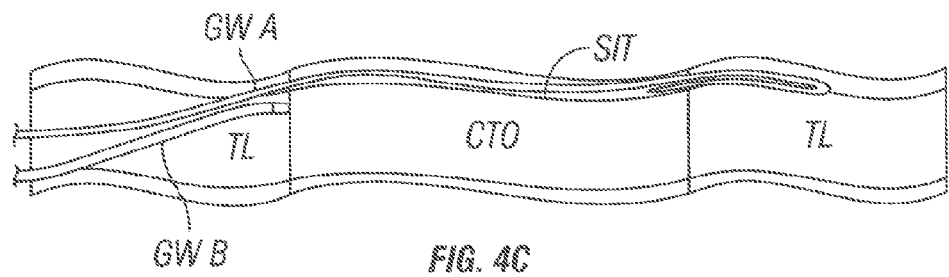
Figures 1, 4C:
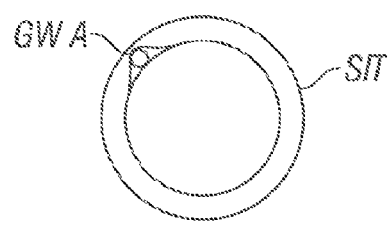
Figures 2, 4C:
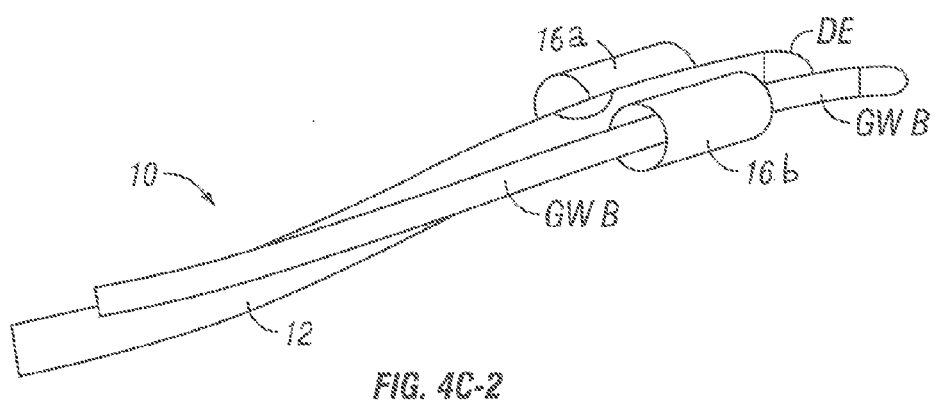
Figure 4D:
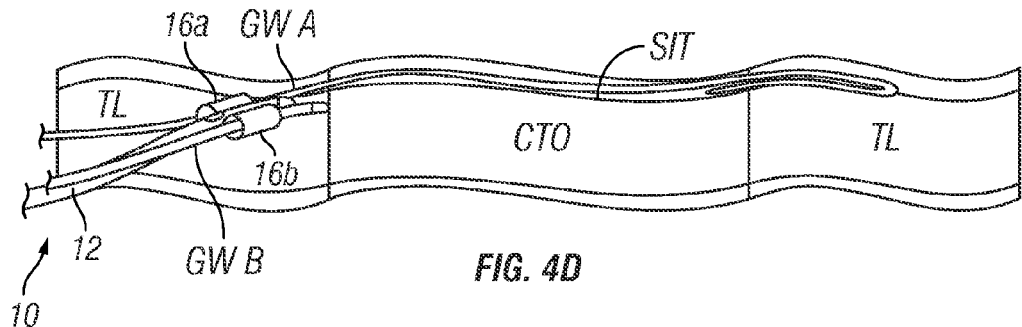
Figures 1, 4D:
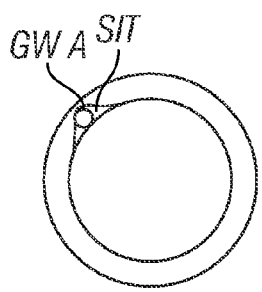

Thereafter, as shown in FIGS. 4C and 4C-1, a second auxiliary guide wire GW B may be advanced to a location just proximal to the obstruction. In one approach, the second auxiliary guide wire GW B is alone advanced to the location just proximal to the obstruction (as seen in FIG. 4C) and, thereafter, the proximal end of the first auxiliary guidewire GW A is inserted into the lumen of the first side tube 16a, the proximal end of the second auxiliary guidewire GW B is inserted into the lumen of the second side tube 16b and the reentry device 10 is then advanced over the previously-inserted first and second auxiliary guidewires GW A, GW B to the position shown in FIG. 4D. In an alternative approach, the distal end of the second auxiliary guidewire GW B is preloaded into or slightly through the lumen of the second side tube 16b as shown in FIG. 4C-2, the proximal end of the first auxiliary guidewire GW A is inserted into the lumen of the first side tube 16a, and the reentry device and accompanying second auxiliary guidewire GW B are then advanced over the first auxiliary guidewire GW A to the position seen in FIG. 4D. Irrespective of which approach is used to arrive at the positioning seen in FIG. 4D, only the first auxiliary guidewire GW A is within the subintimal tract SIT at this stage of the procedure. This is illustrated in FIG. 4D-1.

Figure 4E:
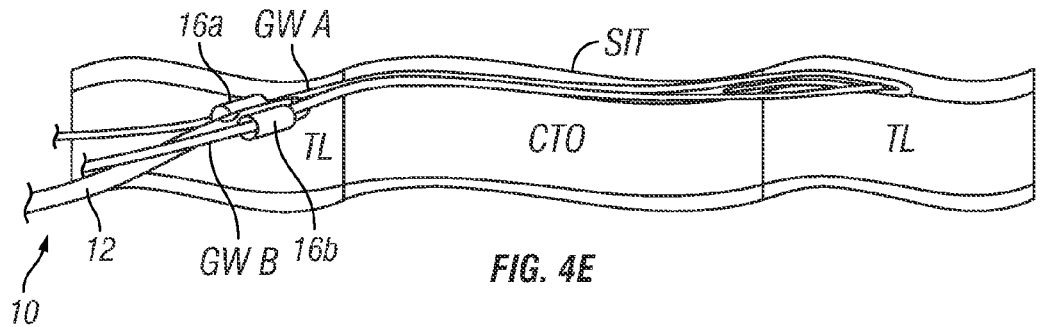
Figures 1, 4E:
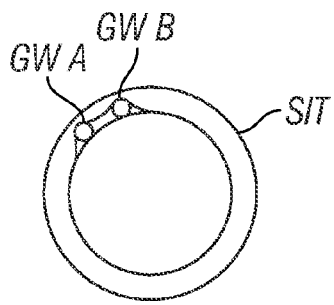

As seen in FIGS. 4E and 4E-1, the distal end of the second auxiliary guidewire GW B is then pushed into the subintimal tract SIT and advanced to the distal extent of that tract SIT next to the first auxiliary guidewire GW A. The reentry device 10 may be maneuvered (e.g., twisted or moved back and forth) to help guide the distal end of the second auxiliary guidewire GW B into the proximal end of the subintimal tract SIT or a separate introducer sheath or guiding catheter may be used to facilitate this in accordance with techniques known in the fields of interventional cardiology and catheter-based vascular interventions.

Figure 4F:
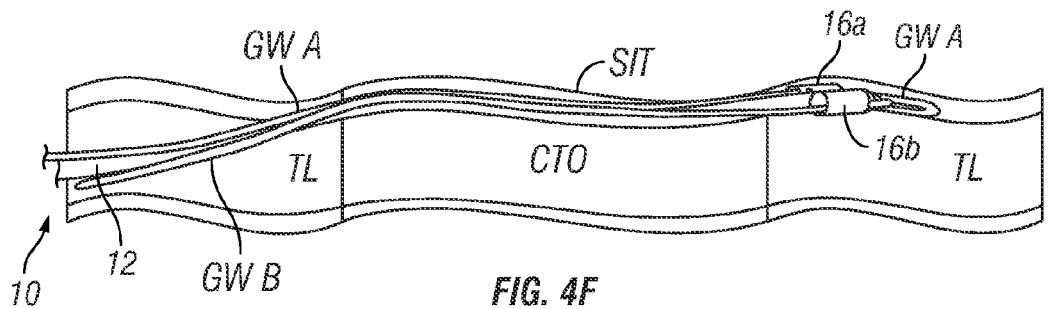
Figures 1, 4F:
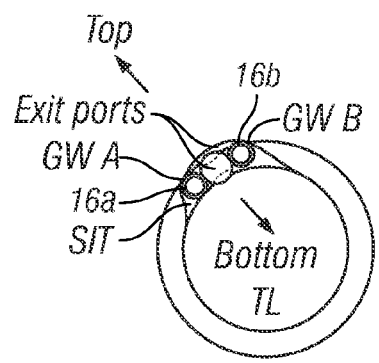

Thereafter, as shown in FIGS. 4F and 4F-1, the reentry device 10 is advanced over the first and second auxiliary guidewires GW A, GW B and through the subintimal tract SIT until it arrives at the position shown in FIG. 4F, i.e. distal to the obstruction CTO. As explained above, due to its shape, the distal portion 14 of the reentry device assumes a rotational orientation within the subintimal tract SIT such that its transverse dimension X extends across the width W of the subintimal tract SIT and its vertical dimension Y extends over the depth D of the subintimal tract SIT. Thus, either the top side outlet aperture 30a or bottom side outlet aperture 30b will necessarily be directed toward the true lumen TL of the vessel.

Figure 4G:
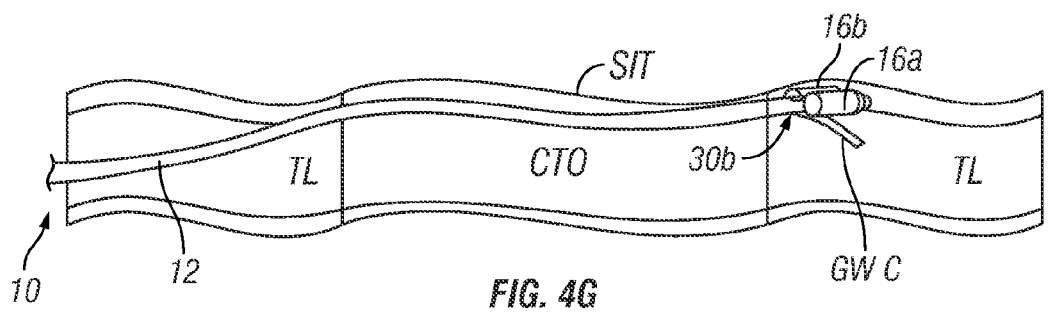
Figures 1, 4G:
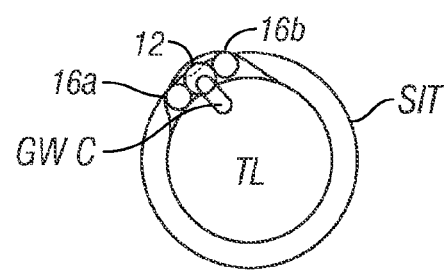

The operator will determine which of the guidewire outlet apertures 30a or 30b is directed toward the true lumen TL. In embodiments that include optional radiopaque markers, such as the above-described markers 17a, 17b, 17a-1, 17b-1, the operator may use fluoroscopic images of those markers to ascertain which of the guidewire outlet apertures 30a or 30b is directed toward the true lumen TL. Thereafter, as shown in FIGS. 4G and 4G-1, a main guidewire GW C is then advanced through the main catheter shaft 12 and out of whichever guidewire outlet aperture 30a, 30b is directed toward the true lumen TL. After exiting the selected guidewire outlet aperture 30a or 30b, the main guidewire GW C is further advanced through the intervening intimal tissue and into the true lumen TL of the artery distal to the obstruction CTO. In instances where the main catheter shaft 12 has a single guidewire lumen, the main guidewire GW C may have a curved distal end to enable the operator to selectively cause the distal tip of the main guidewire GW C to enter the intended guidewire outlet aperture 30a or 30b directed toward the true lumen TL, rather than the other guidewire outlet aperture directed outwardly toward the adventitia A. Alternatively, in instances where the main catheter shaft 12 has two guidewire lumens, one of which leads to top side guidewire outlet aperture 30a and the other of which leads to bottom side guidewire outlet aperture 30b, the operator will advance the main guidewire GW C through whichever of those guidewire lumens leads to the intended guidewire outlet aperture 30a or 30b.

Figure 4H:
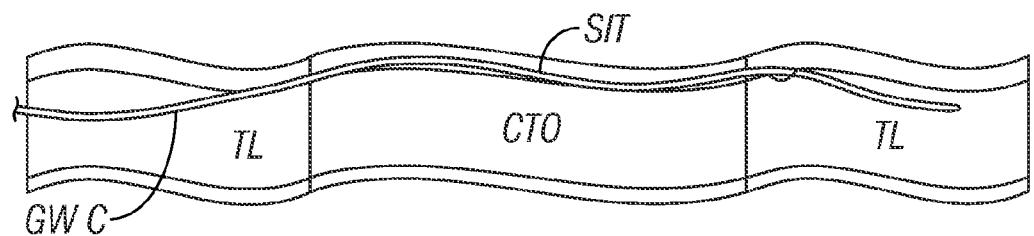

Thereafter, as shown in FIG. 4H, the reentry catheter device 10, the first auxiliary guidewire GW A and the second auxiliary guidewire GW B are removed, leaving the main guidewire GW C in place and extending through the true lumen TL proximal to the obstruction CTO, through the subintimal tract SIT around the obstruction CTO, and back into the true lumen TL distal to the obstruction.

Reentry Catheter Having a Single Side Tube

FIGS. 5A through 5G show an alternative procedure using an embodiment of the reentry catheter device 10a that has only a single side tube 16. This single side tube reentry catheter device 10a may have both top and bottom guidewire outlet apertures 30a, 30b as described above or, alternatively, it may have only a single guidewire outlet aperture 30 located in either the top or bottom side of the main catheter shaft 12.

Figure 5A:
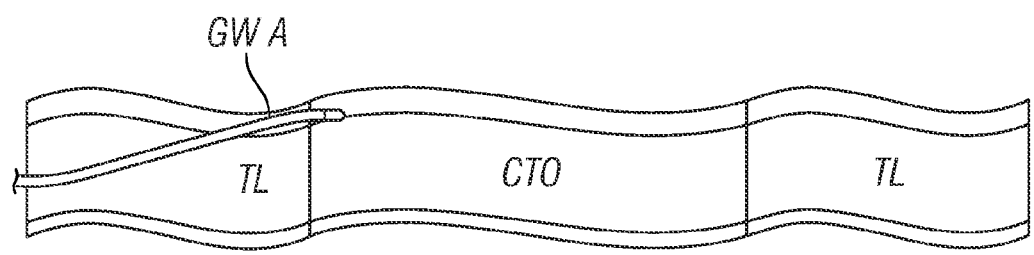
Figures 1, 5A:
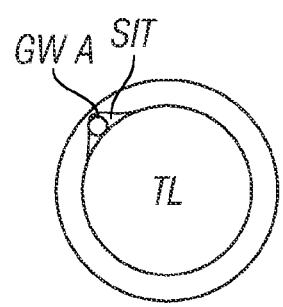
Figure 5B:
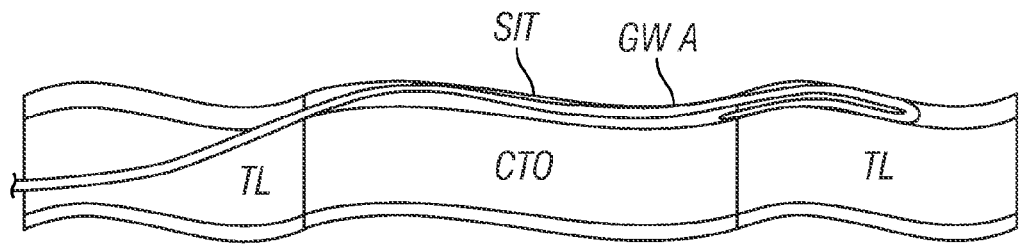
Figures 1, 5B:
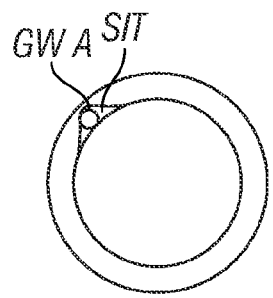

In this procedure, a first auxiliary guidewire GW A is advanced through the vasculature and into the true lumen TL of the obstructed artery, just distal to a total obstruction CTO. As illustrated in FIGS. 5A and 5A-1, the distal end of the first auxiliary guidewire GW A is then pushed into the wall of the artery, adjacent to the proximal end of the obstruction CTO, thus beginning the formation of a subintimal tract SIT within the artery wall. Thereafter, as shown in FIGS. 5B and 5B-1, the first auxiliary guidewire GW A is further advanced within the artery wall, causing a distal portion of the first auxiliary guidewire GW A to double over in loop-like fashion and extending the subintimal tract SIT past the obstruction CTO. As explained above, formation of the subintimal tract SIT in this manner causes the subintimal tract SIT to have a width W that is greater than its depth D (see FIG. 3).

Figure 5C:
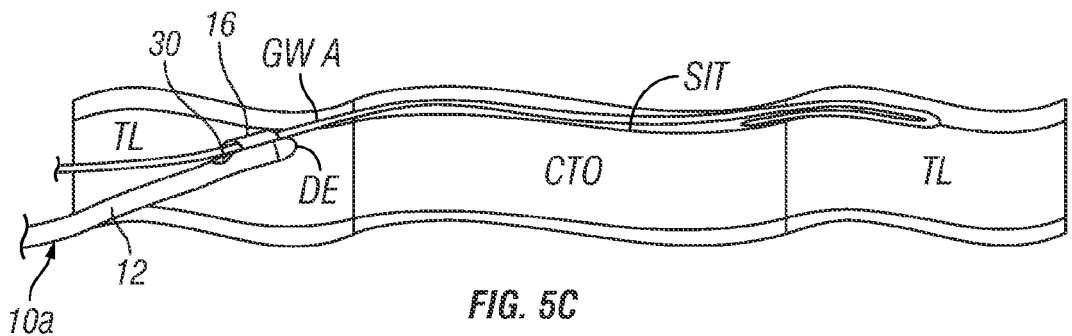
Figures 1, 5C:
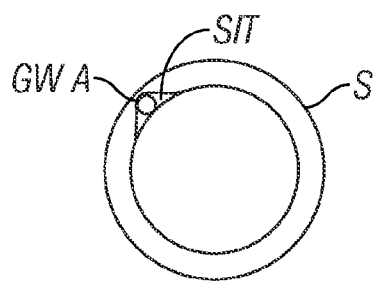

Thereafter, the proximal end of the first auxiliary guidewire GW A is inserted into the lumen of the side tube 16 and the reentry device 10a is advanced over the first auxiliary guidewire GW A to a position proximal to the obstruction CTO, as shown in FIGS. 5C and 5C-1.

The auxiliary guidewire GW A is then used as a fulcrum and the reentry device 10a is advanced over the auxiliary guidewire GW A and into the subintimal tract SIT to the position shown in FIGS. 5D and 5D-1. Even though this embodiment of the reentry device 10a has only a single side tube 16, its distal portion still has a transverse dimension that is greater than its vertical dimension. Thus, the distal portion of this device will assume a rotational orientation within the subintimal tract whereby its transverse dimension extends across the subintimal tract SIT and either the top side or bottom side of the main catheter shaft 12 is positioned adjacent to the intimal tissue and true lumen TL. If this procedure is being performed with a reentry device 10a that has both a top side guidewire outlet aperture 30a and a bottom side guidewire outlet aperture 30b, then one of those guidewire outlet apertures 30a, 30b will necessarily be directed toward the true lumen TL of the artery and the operator may selectively advance a main guidewire GW C out of whichever guidewire outlet aperture 30a, 30b is directed toward the true lumen TL. In such instances, if the main catheter shaft 12 has only a single guidewire lumen, the main guidewire GW C may preferably have a curved distal end to enable the operator to selectively cause the distal tip of the main guidewire GW C to enter the intended guidewire outlet aperture 30a or 30b directed toward the true lumen TL. Alternatively, if the main catheter shaft 12 has two guidewire lumens, one of which leads to top side guidewire outlet aperture 30a and the other of which leads to bottom side guidewire outlet aperture 30b, the operator will advance the main guidewire GW C through whichever of those guidewire lumens leads to the intended guidewire outlet aperture 30a or 30b.

However, if procedure is being performed with a reentry device 10a that has only a single guidewire outlet aperture 30 located in either the top or bottom side of the main catheter shaft 12, the operator will determine whether that sole guidewire outlet aperture 30 is directed toward the true lumen TL as desired or, alternatively, in the opposite direction toward the adventitia as illustrated in FIG. 5E. Radiopaque or otherwise imageable markers may be provided on the reentry device 10a to facilitate the operator's determination of which direction the sole guidewire outlet aperture 30 is directed. If it is determined that the sole guidewire outlet aperture 30 is directed outwardly toward the adventitia as shown in FIG. 5E, then it will be necessary to rotate the distal portion of the reentry device 10a within the subintimal tract SIT, as shown in FIGS. 5E-1, 5E-2 and 5E-3, to thereby redirect the sole guidewire outlet aperture 30 toward the true lumen TL.

Figure 5F:
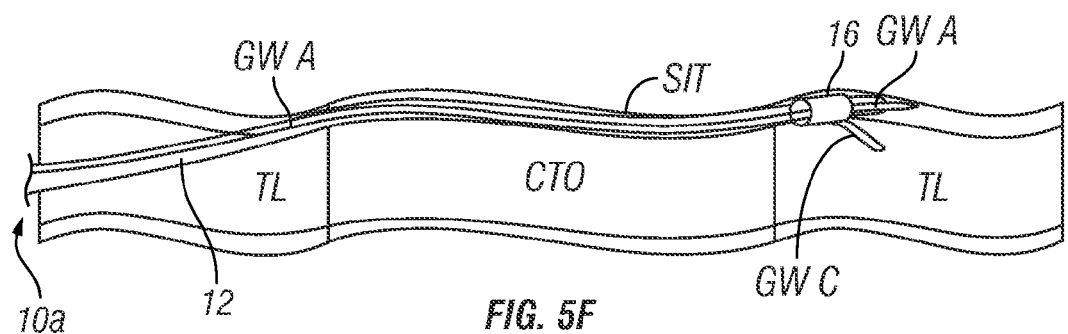
Figures 1, 5F:
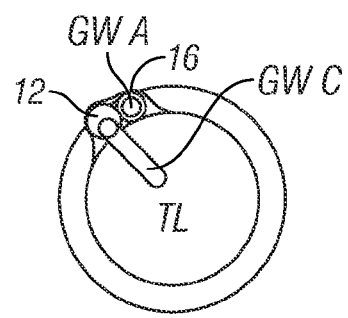

With the guidewire outlet aperture 30 directed toward the true lumen TL, a main guidewire GW C is then advanced through the main reentry catheter shaft 12, out of the guidewire outlet aperture 30, through the intervening intimal tissue and into the true lumen TL distal to the obstruction CTO, as shown in FIGS. 5F and 5F1.

Figure 5G:
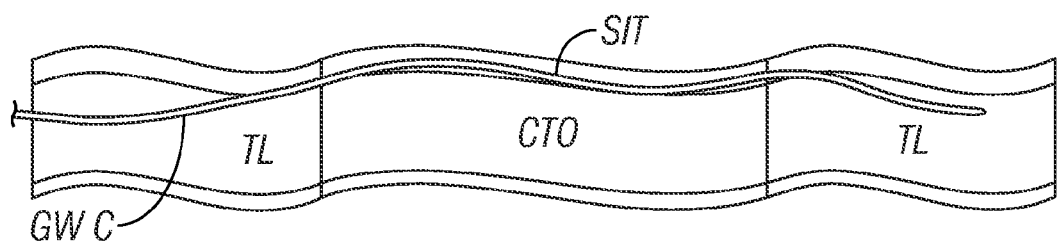

Thereafter, as shown in FIG. 5G, the reentry catheter device 10a and the first auxiliary guidewire GW A are removed, leaving the main guidewire GW C in place such that it extends through the true lumen TL proximal to the obstruction CTO, through the subintimal tract SIT around the obstruction CTO, and back into the true lumen TL distal to the obstruction.

Figure 6A:
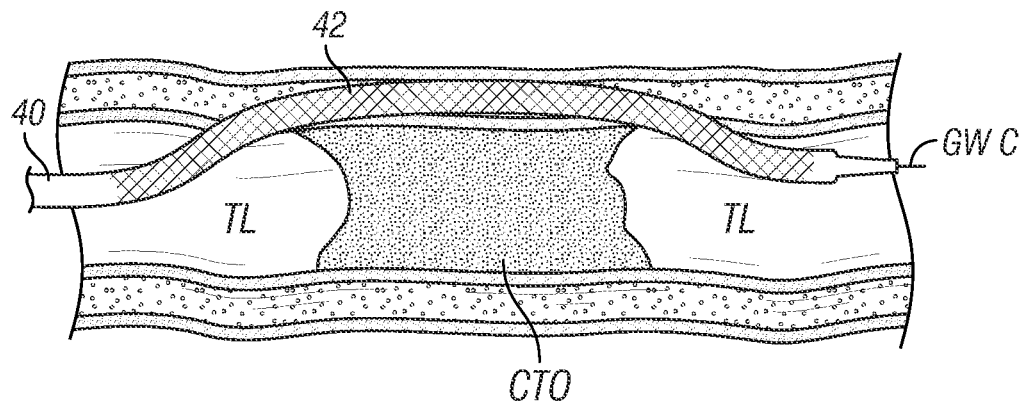
FIGS. 6A and 6B show examples of working devices and method steps that may be used in conjunction with the methods illustrated in FIG. 4A through 4H or 5A through 5G to complete a transluminal catheter-based bypass of a CTO in an artery.
Figure 6B:
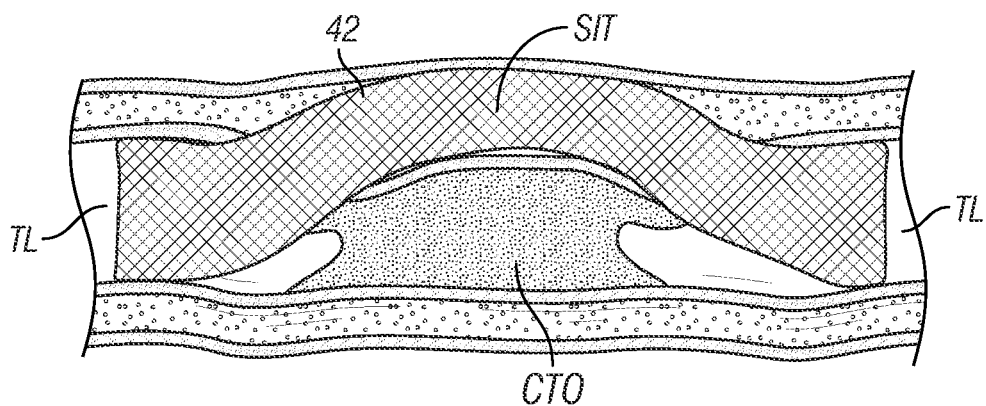

Irrespective of whether reentry of the main guidewire GW C into the true lumen TL is accomplished using the dual side tube reentry catheter device 10 or the single side tube reentry catheter device 10a, the result is that the main guidewire GW C becomes positioned in the manner shown in either FIG. 4H or FIG. 5G. Once the main guidewire GW C has been so positioned, the main guidewire GW C is then useable to guide the subsequent advancement of one or more additional working devices (e.g., balloon catheters, atherectomy catheters, stent delivery catheters, laser catheters, etc.) to enlarge (e.g., dilate, debulk, bore, stent, etc.) the subintimal tract SIT, thereby establishing a patent blood flow route around the obstruction CTO. FIGS. 6A and 6B show one non-limiting example of how enlargement of the subintimal tract SIT may be accomplished. In this example, the working device(s) used for enlargement of the subintimal tract SIT comprise a balloon catheter 40 and a stent 42. With its balloon in a deflated state and the stent 42 mounted over the balloon, the balloon catheter 40 is advanced over the main guidewire GW C to a position where one end of the stent 42 is in the true lumen TL proximal to the obstruction CTO and the other end of the stent 42 is in the true lumen TL distal to the obstruction CTO. The balloon of the balloon catheter 40 is then inflated to dilate the subintimal tract SIT and expand the stent 42. Thereafter, as seen in FIG. 6B, the balloon of balloon catheter 40 is deflated and the balloon catheter 40 is removed, leaving the stent 42 in an expanded configuration and creating a stented, subintimal blood flow channel around the obstruction CTO.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A blood vessel lumen reentry device comprising:
   a catheter having a distal end, a right side, a left side, a top side and a bottom side;
   a first guidewire exit port located in the bottom side of the catheter a spaced distance from its distal end;
   a second guidewire exit port located in the top side of the catheter a spaced distance from its distal end;
   a lumen extending from the distal end of the catheter to at least the first and second guidewire exit ports;
   a rotational orientation indicator useable for determining the rotational position of the guidewire exit port when positioned within the blood vessel of a human or animal subject;
   a side tube on either the right or left side of the catheter adjacent to the first and second guidewire exit ports, said side tube having a proximal end opening, a through lumen and a distal end opening.

2. A device according to claim 1 wherein the distal end of the catheter is closed.

3. A device according to claim 1 wherein the rotational orientation indicator comprises a marker which, when imaged by an imaging device, provides an indication of the rotational position of the guidewire exit port.

4. A method for using a reentry device according to claim 1 to facilitate bypassing an obstruction in a blood vessel that has a true lumen and a blood vessel wall, said method comprising the steps of:
   advancing a first guidewire, which has a proximal end and a distal end, through the lumen of the blood vessel proximal to the obstruction and into the blood vessel wall adjacent to the obstruction so as to create a subintimal tract which is separate from the true lumen of the blood vessel, said subintimal tract extending past the obstruction and the distal end of the first guidewire being positioned within the subintimal tract at a location distal to the obstruction;
   inserting the proximal end of the first guidewire into the distal end opening of the side tube and advancing the device of claim 1 over the first guidewire and into the subintimal tract to a location where the guidewire exit port is located distal to the obstruction;
   using the rotational orientation indicator to determine the rotational position of the guidewire exit port within the subintimal space;
   adjusting the rotational orientation of the reentry device, if necessary, to cause the guidewire exit port to be directed toward the true lumen of the blood vessel;
   advancing a second guidewire through the lumen of the catheter, out of the guidewire exit port and into the true lumen of the blood vessel, distal to the obstruction;
   removing the first guidewire and the reentry device, leaving the second guidewire in place such that the second guidewire extends through the true lumen proximal to the obstruction, through the subintimal tract and back into the true lumen distal to the instruction; and
   advancing one or more working devices over the second guidewire to dilate the subintimal tract thereby creating a blood flow channel around the obstruction.

5. A method for using a reentry device according to claim 1 to facilitate bypassing an obstruction in a blood vessel that has a true lumen and a blood vessel wall, said method comprising the steps of:
   loading a distal portion of a first guidewire into the side tube and advancing the device of claim 1 through the lumen of the blood vessel proximal of the obstruction;
   advancing the first guidewire into a subintimal tract created within the wall of the blood vessel, said subintimal tract being separate from the true lumen of the blood vessel and extending past the obstruction, and advancing the reentry device over the first guidewire to a location where its guidewire exit port is located distal to the obstruction;
   using the rotational orientation indicator to determine the rotational position of the guidewire exit port within the subintimal space;

adjusting the rotational orientation of the reentry device, if necessary, to cause the guidewire exit port to be directed toward the true lumen of the blood vessel;

advancing a second guidewire through the lumen of the catheter, out of the guidewire exit port and into the true lumen of the blood vessel, distal to the obstruction;

removing the first guidewire that is positioned within the subintimal tract and the reentry device, leaving the second guidewire in place such that the second guidewire extends through the true lumen proximal to the obstruction, through the subintimal tract around the obstruction and back into the true lumen distal to the instruction; and advancing one or more working devices over the second guidewire to dilate the subintimal tract thereby creating a blood flow channel around the obstruction.

6. A method according to claim 5 wherein the obstruction is a chronic total obstruction.

7. A method according to claim 5 wherein said at least one working device comprises a balloon for dilating the subintimal tract.

8. A method according to claim 7 wherein said at least one working device further comprises a stent for stenting the dilated subintimal tract.

9. A blood vessel lumen reentry device comprising:
a catheter having a distal end, a right side, a left side, a top side and a bottom side;
a lumen extending through the catheter;
a first guidewire exit port located in the top side of the catheter a spaced distance from its distal end;
a second guidewire exit port located in the bottom side of the catheter a spaced distance from its distal end;
a rotational orientation indicator useable for determining the rotational positions of the first and second guidewire exit ports when positioned within a blood vessel of a human or animal subject;
a first side tube attached to the right side of the catheter adjacent to the first and second exit ports, said first side tube having a proximal end opening, a through lumen and a distal end opening; and
a second side tube attached to the left side of the catheter adjacent to the first and second exit ports, said second side tube having a proximal end opening, a through lumen and a distal end opening.

10. A device according to claim 9 wherein the rotational orientation indicator comprises a marker which, when imaged by an imaging device, provides an indication of the rotational positions of the first and second guidewire exit ports.

11. A device according to claim 9 wherein the first and second guidewire exit ports are at longitudinally spaced-apart locations.

12. A device according to claim 9 wherein the distal end of the catheter is closed.

13. A device according to claim 9 wherein the rotational orientation indicator comprises a marker which, when imaged by an imaging device, provides an indication of rotational positions of the first and second guidewire exit ports.

14. A method for using a reentry device according to claim 13 to facilitate bypassing an of an obstruction in a blood vessel that has a true lumen and a blood vessel wall, said method comprising the steps of:
causing a first guidewire and a second guidewire to extend through the true lumen of the blood vessel proximal to the obstruction and to create a subintimal tract within the wall of the blood vessel, said subintimal tract being separate from the true lumen of the blood vessel and extending past the obstruction;

advancing the reentry device, with the first and second side tubes tracking over the first and second guidewires respectively, to a location where the first and second guidewire exit ports are located within the subintimal tract distal to the obstruction;

using the rotational orientation indicator to determine which of the first and second guidewire exit ports is directed toward the true lumen of the blood vessel;

advancing a third guidewire through the lumen of the catheter, out of whichever guidewire exit port is determined to be directed toward the true lumen of the blood vessel and into the true lumen of the blood vessel, distal to the obstruction;

removing the first guidewire, the second guidewire and the reentry device, leaving the third guidewire in place such that the third guidewire extends through the true lumen proximal to the obstruction, through the subintimal tract, and back into the true lumen distal to the instruction; and advancing one or more working devices over the third guidewire to dilate the subintimal tract thereby creating a blood flow channel around the obstruction.

15. A method according to claim 14 wherein the first guidewire was used to create the subintimal tract and then allowed to remain within the subintimal tract.

16. A method according to claim 14 wherein:
after the first and second guidewires have been advanced into the subintimal tract, the proximal ends of the first and second guidewires are inserted into the distal end openings of the first and second side tubes of the reentry device; and
the reentry device is then advanced, with the first and second side tubes tracking over the first and second guidewires, to said location within the subintimal tract.

17. A method according to claim 14 wherein:
after the first guidewire has been advanced into the subintimal tract, the proximal end of the first guidewire is inserted into the distal end opening of the first side tube;
the distal end of the second guidewire is inserted into the proximal end opening of the second side tube;
the reentry device and second guidewire are advanced, with the first side tube tracking over the first guidewire, to a location near the location at which the first guidewire enters the subintimal tract;
the second guidewire is then advanced through the second side tube and into the subintimal tract along side the first guidewire; and
the reentry device is then further advanced, with the first and second side tubes tracking over the first and second guidewires, to said location within the subintimal tract.

18. A method according to claim 14 wherein the obstruction is a chronic total obstruction.

19. A method according to claim 14 wherein said at least one working device comprises a balloon for dilating the subintimal tract.

20. A method according to claim 19 wherein said at least one working device further comprises a stent for stenting the dilated subintimal tract.

21. A blood vessel lumen reentry device comprising:
a catheter having a distal end and a side wall;
a first guidewire exit port formed at a first location in the side wall of the catheter a spaced distance from its distal end;
a second guidewire exit port formed at a second location in the side wall of the catheter a spaced distance from its distal end;
a lumen extending from the distal end of the catheter to at least the guidewire exit port;

a rotational orientation indicator useable for determining the rotational position of the guidewire exit port when positioned within the blood vessel of a human or animal subject;

a side tube extending along a portion of the catheter side wall such that the first guidewire exit port is located above the side tube and the second guidewire exit port is located below the side tube, said side tube having a proximal end opening, a through lumen and a distal end opening.

* * * * *